United States Patent [19]

Marchegiano et al.

[11] Patent Number: 4,641,256

[45] Date of Patent: Feb. 3, 1987

[54] SYSTEM AND METHOD FOR MEASURING ENERGY TRANSMISSION THROUGH A MOVING APERTURE PATTERN

[75] Inventors: Joseph E. Marchegiano, Wilmington, Del.; Anthony S. Baran, Lancaster, Pa.

[73] Assignee: RCA Corporation, Princeton, N.J.

[21] Appl. No.: 678,211

[22] Filed: Dec. 4, 1984

[51] Int. Cl.⁴ ............ G01N 21/00; G01N 21/84
[52] U.S. Cl. .................... 364/525; 356/237; 356/430
[58] Field of Search ........... 356/429, 430, 432, 435, 356/444, 445, 237, 239, 355, 375; 364/525

[56] References Cited

U.S. PATENT DOCUMENTS

| | | | |
|---|---|---|---|
| 3,954,337 | 5/1976 | Ragland et al. | 356/355 |
| 4,124,300 | 11/1978 | Mead et al. | 356/429 |
| 4,282,511 | 8/1981 | Southgate et al. | 356/430 |
| 4,289,406 | 9/1981 | Maddox | 356/429 |
| 4,292,672 | 9/1981 | Southgate et al. | 356/239 |
| 4,330,775 | 5/1982 | Iwamoto et al. | 356/237 |
| 4,349,880 | 9/1982 | Southgate et al. | 356/237 |
| 4,400,233 | 8/1983 | Rangachar et al. | 156/626 |
| 4,408,883 | 10/1983 | Iwamoto et al. | 356/355 |
| 4,560,280 | 12/1985 | Iwamoto et al. | 356/375 |

Primary Examiner—Russell E. Adams
Attorney, Agent, or Firm—E. M. Whitacre; D. H. Irlbeck; L. L. Hallacher

[57] ABSTRACT

A system for measuring the energy transmission through a moving aperture pattern includes a CCD (charge coupled device) sensor having at least one row of pixels arranged perpendicular to the direction of motion. An encoder responds to the motion and provides count pulses. For each count pulse, specific pixels are addressed to establish a plurality of inspection areas for the aperture pattern through which energy transmission is measured. The transmission is averaged for all the inspection areas to determine the acceptability of the aperture pattern.

21 Claims, 8 Drawing Figures

SYSTEM AND METHOD FOR MEASURING ENERGY TRANSMISSION THROUGH A MOVING APERTURE PATTERN

BACKGROUND

This invention relates generally to the measurement of energy transmission through an aperture pattern in a longitudinally moving strip of material and particularly to the measurement of light through the aperture patterns in shadow masks for kinescopes.

In the manufacture of shadow masks for color television kinescopes, a roll of flat material is coated with a photoresist material and is subsequently photoexposed to form a series of aperture patterns, and the peripheries of the shadow masks, in the photoresist material. The unexposed photoresist material is washed away leaving bare metal. The strip of material is subjected to an acid etching process in which the bare metal is removed to form the apertures, and partially etched peripheries used to remove the shadow masks from the strip of material. After the etching is completed, the transmission of energy through the aperture pattern is measured to verify that the shadow masks are suitable for the intended use. The measurement of light transmission through the aperture patterns typically is accomplished by shining a known intensity of light through the apertures and noting the percentage of light which passes through the apertures. The acid etching and the light transmission measurements typically are made while the strip of material is pulled longitudinally along a conveyor line. Because of the long length of the strip, there is a tendency for the strip to move transversely back and forth perpendicular to the longitudinal motion. The areas of the apertures vary along the transverse dimension of the pattern and for this reason, accuracy of the light transmission measurement requires that all measurements be made at the same transverse position of the aperture pattern. Accordingly, transverse motion causes a degradation of the measurement accuracy. It is extremely difficult, if not impossible, to restrain the long strip to prevent the transverse motion.

One technique of overcoming the adverse effects of the transverse motion includes movably mounting the measuring device to track the transverse motion and maintain a substantially constant relative position between the measuring device and the aperture pattern. This technique suffers the disadvantage of being complex and expensive. Therefore, there is a need for a system in which the sensor is permanently mounted and the undesired motion is compensated.

SUMMARY

A system for measuring energy transmission through an aperture pattern in a longitudinally moving opaque strip of material including means for scanning energy transversely across the strip. A CCD (charge coupled device) sensor having at least one row of pixels is arranged substantially perpendicular to the strip. A particular pixel of the CCD is centered over the strip when the strip is located at an optimum location. The system includes means for defining inspection areas within the aperture pattern where energy transmission is to be measured. The inspection areas are defined by preselected pixels of the CCD when the CCD is scanned by energy passing through the inspection area. An encoder is responsive to the longitudinal motion and provides count pulses. A counter is responsive to the count pulses, whereby the inspection areas are scanned on preselected counts. The charge levels on the preselected CCD pixels are indicative of energy transmission through the aperture pattern. An adder adds the pixel levels for each inspection area, and provides the energy transmission through each of the inspection areas.

DETAILED DESCRIPTION

Figure 1:
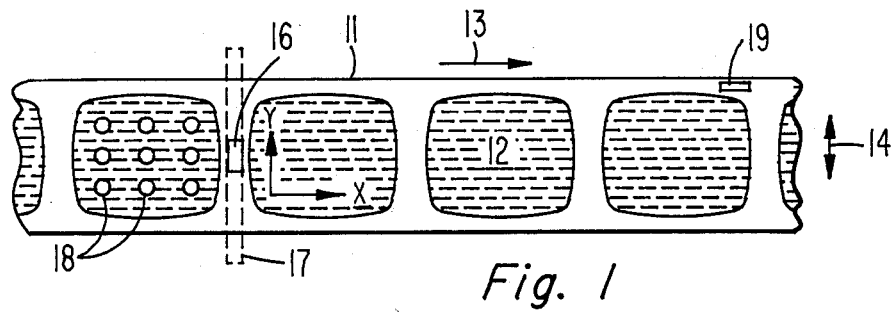
FIG. 1 is a top view showing the motions and scanning of the aperture patterns in a shadow mask.
Figure 2:
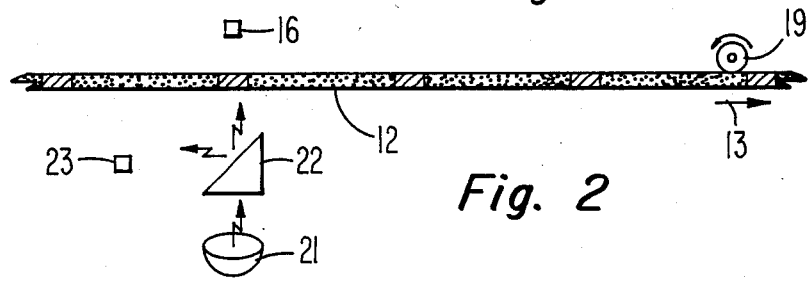
FIG. 2 is a side view of FIG. 1.

In FIG. 1, an opaque strip of material 11 has been etched to include a plurality of aperture patterns 12 through which the transmission of light is to be measured. The aperture patterns 12 can be, for example, shadow masks used as the color selection electrode in kinescopes. The aperture patterns 12 preferably are centered between the edges of the strip 11. However, some variation in the transverse positioning occurs because of imprecision in the photographic processing. The strip 11 moves longitudinally, as indicated by the arrow 13, and because of the substantial length the strip also moves transversely, as indicated by the arrow 14. A CCD sensor 16 is accurately centered with respect to the longitudinal center line of the strip 11 when the strip is in an optimum position. Accordingly, the CCD is also centered over the aperture pattern 12, when the pattern is transversely centered in the strip 11. The CCD sensor 16 can be a linear array of pixels having one pixel accurately centered with respect to the center line of the strip 11 when the strip is in the optimum position. The linear CCD is substantially perpendicular to the longitudinal axis of the strip 11. Alternatively, the CCD 16 can be a planar array having one row, or one column, of pixels arranged substantially perpendicular to the center line of the strip 11. The CCD is arranged in a camera of known type having an optical system whereby the entire width of the strip 11 is imaged onto the CCD. The side of the strip opposite the CCD is transversely scanned, as indicated by the phantom lines 17, by a light source 21 and a prism 22 (FIG. 2). Such scanning systems also are commercially available.

The transmission of light through the aperture patterns 12 is measured through a plurality of measuring areas 18. These areas are defined for selected locations within the aperture patterns 12 and are the same for every shadow mask of a particular type. The number, and positions of the measuring areas can vary for different types of shadow masks. An encoder 19 is arranged to respond to the longitudinal motion of the strip 11 to generate count pulses. The count pulses are used to detect the alignment of the inspection areas 18 with the CCD 16. The count pulses are generated at a rate related to the motion of the strip 11. Accordingly, the first inspection area is known to begin at some exact count after the leading edge of the aperture pattern is detected. The inspection areas are transversely defined by the longitudinal sides of the patterns and are known to coincide with particular pixels of the CCD when the strip is in the optimum position and when the aperture pattern is centered on the strip 11.

In FIG. 2, the light source 21 provides light to a light splitting prism 22. Accordingly, light passes through the aperture patterns 12 and impinges upon the CCD 16 when an aperture pattern is present between the prism 22 and the CCD 16. Additionally, an equal amount of light directly impinges upon another CCD 23. The lensing, the light and the scanning systems are standard, commercial items. The use of the two CCDs 16 and 23 permits the calibration and normalization of the system to accommodate changes in the light due to the accumulation of dirt or to changes in the brightness of the light emanating from the source 21.

Figure 4:
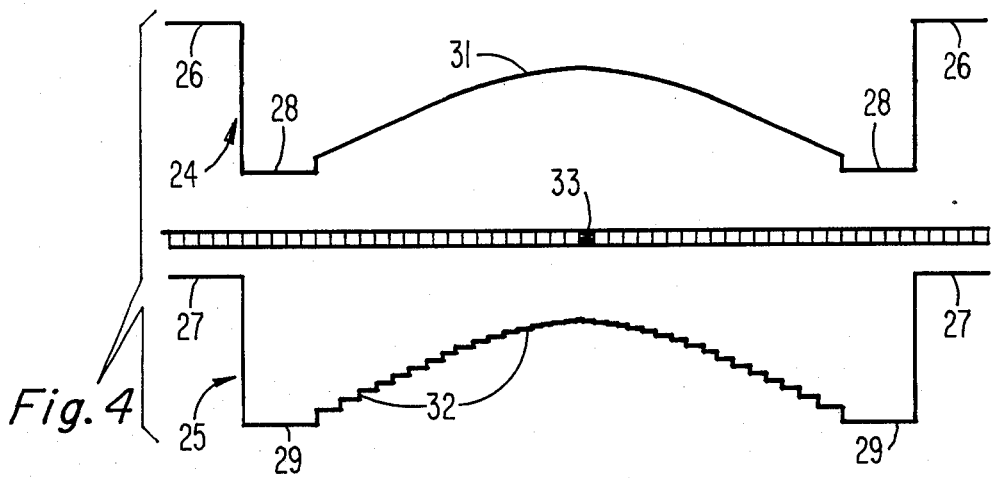
FIG. 4 shows the variation of light transmission through the shadow mask and the response levels of the CCD pixels.

In FIG. 4, the waveform 24 represents the light impinging upon the pixels of the CCD sensor 16. The waveform 25 represents the charge levels on the CCD pixels. The pixels which receive light beyond the edges of the strip 11 are fully illuminated with high intensity light indicated by the level 26. Thus, those pixels are charged to the high level indicated by the level 27. The strip 11 is solid material between the aperture patterns 12 and the edges of the strip. Therefore, no light is received by the pixels which correspond to the opaque areas, which are indicated by the low levels 28. These pixels are uncharged, as indicated by the low levels 29. The curved portion 31 of the waveform 24 represents the transmission of light through the aperture patterns 12 and accordingly the pixels of the CCD 16 which receive energy through the aperture pattern are charged to levels proportioned to the impinging light, as indicated by portion 32 of the waveform 25. Typically, approximately 30% of the light passes through the aperture patterns. Accordingly, the peaks of levels 31 and 32 are approximately 30% of the 26 and 27 levels.

The CCD sensor 16 is accurately centered over the strip 11 when the strip is in an optimum position. Also, the transverse edges of the aperture patterns 18 are easily detectable. Accordingly, one pixel, such as pixel 33, is accurately centered over the longitudinal strip 11. For this reason, for a particular mask size, the number of pixels on each side of the center pixel 33 which are illuminated when the strip 11 is centered is known. Accordingly, when different numbers of pixels are illuminated on the two sides of the center pixel 33 either, or both, a transverse movement of the strip 11, or miscentering of the pattern on the strip 11 is indicated and the displacement can be calculated. This information is used to compensate for the miscentering of the aperture pattern 18 with respect to the CCD sensor 16 in a manner described hereinafter.

Figure 3:
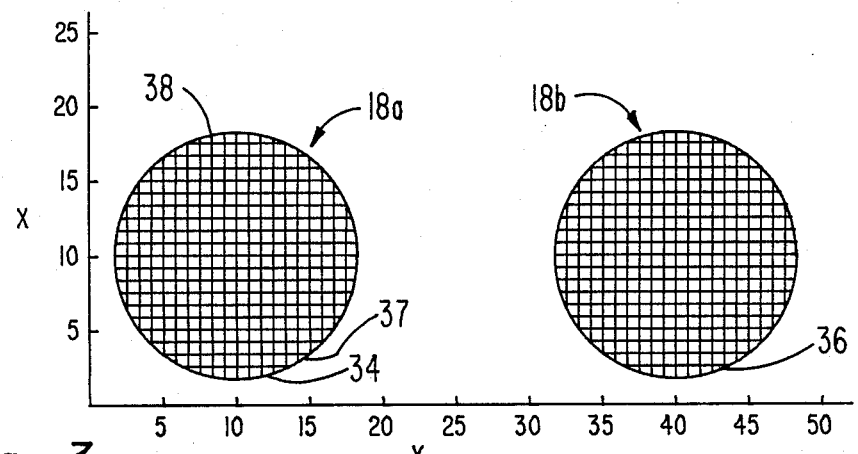
FIG. 3 shows how the CCD pixels are addressed to form inspection areas in the shadow mask aperture patterns.

FIG. 3 shows how the inspection areas 18 of FIG. 1 are defined utilizing the pixels of the CCD 16 and the count pulses from the encoder 19. In FIG. 3, the X axis is vertical and corresponds to longitudinal motion of the strip 11, as shown in FIG. 1. The Y axis is parallel to the linear CCD, or to the utilized row of pixels when a planar CCD array is used. In FIG. 1, nine of the inspection areas 18 are shown. In FIG. 3, two of these areas 18a and 18b are shown in more detail and each square represents one CCD pixel. The inspection areas 18 are defined by addressing particular pixels of the CCD for each count pulse received from the encoder 19. Thus, in FIG. 3, the first portion 34 of the area 18a is defined by addressing pixels which are known to be illluminated when the strip is perfectly centered. For example, the first portion 34 of the area 18a is defined as being a selected number of count pulses from the leading edge of an aperture pattern 12. Accordingly, when the first transition from the low level 29 to the higher level 32 (FIG. 4) is detected, the selected number of the count pulses 19 establishes the X-position of the first portion 34 of the inspection area 18a. The same number of count pulses can be utilized to define a first portion 36 of the inspection area 18b. When the aperture pattern 18a is perfectly centered with respect to the CCD 16, the portion 34 of the inspection area 18a will be composed of known pixels, for example, 5 to 13. Accordingly, the energy levels of those pixels are the first used in measuring light transmission through the area 18a. When inspection area 18b commences on the same count pulse count as the area 18a the pixels 35 to 43, for example, are utilized to define the first portion 36 of the inspection area 18b. When the center pixel 33 is offset from the center, the pixels which are utilized in measuring the light transmission are also shifted. For example, when the center of the aperture pattern 12 is shifted four pixels to the right of the center pixel 33 the pixels used are shifted four pixels to the right. Thus, pixels 9 to 17 would be used in place of 5 to 13, as used in the example above. The shift is utilized for all the measurement areas in the aperture pattern. The next portion 37 of the inspection area 18a is defined by a higher number of count pulses from the encoder 19. The portion 37 also spans more pixels of the CCD than the portion 34. Accordingly, for this portion of the inspection area a total of ten pixels, for example, is addressed during the transfer of data from the CCD array. This operation continues until the last portion 38 of the inspection area 18a is completed. The longitudinal, or X, dimension of the inspection area 18a is selected simply by selecting the number of count pulses from the encoder 19 to be used. No data are considered until the first portion of the next set of inspection areas is encountered in accordance with the preselected number of count pulses from the encoder 19. Accordingly, the transverse, or Y, dimension of the inspection areas 18 are defined by addressing particular pixels for each portion of the inspection areas. The encoder 19 is responsive to the longitudinal motion of the strip 11 and for this reason any variations in the speed of the strip are automatically compensated because the count pulses are generated as a function of distance rather than a function of velocity.

Figure 5A:
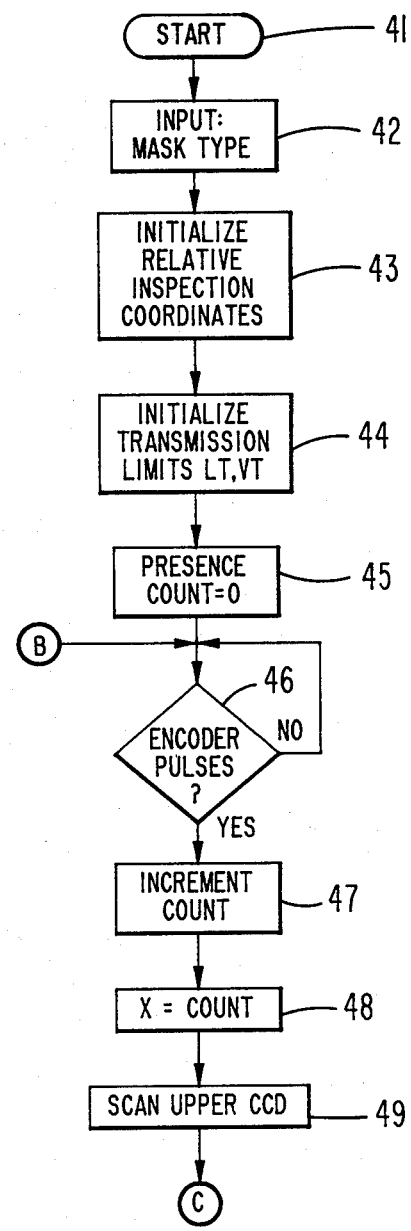
FIGS. 5a to 5d are a flow chart of a preferred embodiment.

In FIG. 5a, the calculation of the transmission through one of the inspection areas 18 (FIG. 1) starts at step 41. At step 42 the type of mask is input to the system. The mask type is needed because the number and locations of the inspection areas can vary for different sizes and types of shadow masks. At step 43, the inspection area coordinates are initialized. This constitutes selecting the number of inspection areas and also defining the inspection pixels and encoder count pulses. The upper and lower transmission limits are initialized at step 44. An acceptable shadow mask has a transmission capability which is within predefined limits. The lower limit assures that the apertures are not too small, or nonexistant, and the upper limit assures that the apertures are not too large. The counter which counts the count pulses from the encoder 19 is set to zero at step 45. At step 46, the encoder pulses are sensed and when no pulses are present the system simply loops back until pulses are detected. The count pulses are incremented at step 47 and are assigned to the X coordinate at step 48.

The upper CCD is scanned through the aperture pattern at step 49.

Figure 5B:
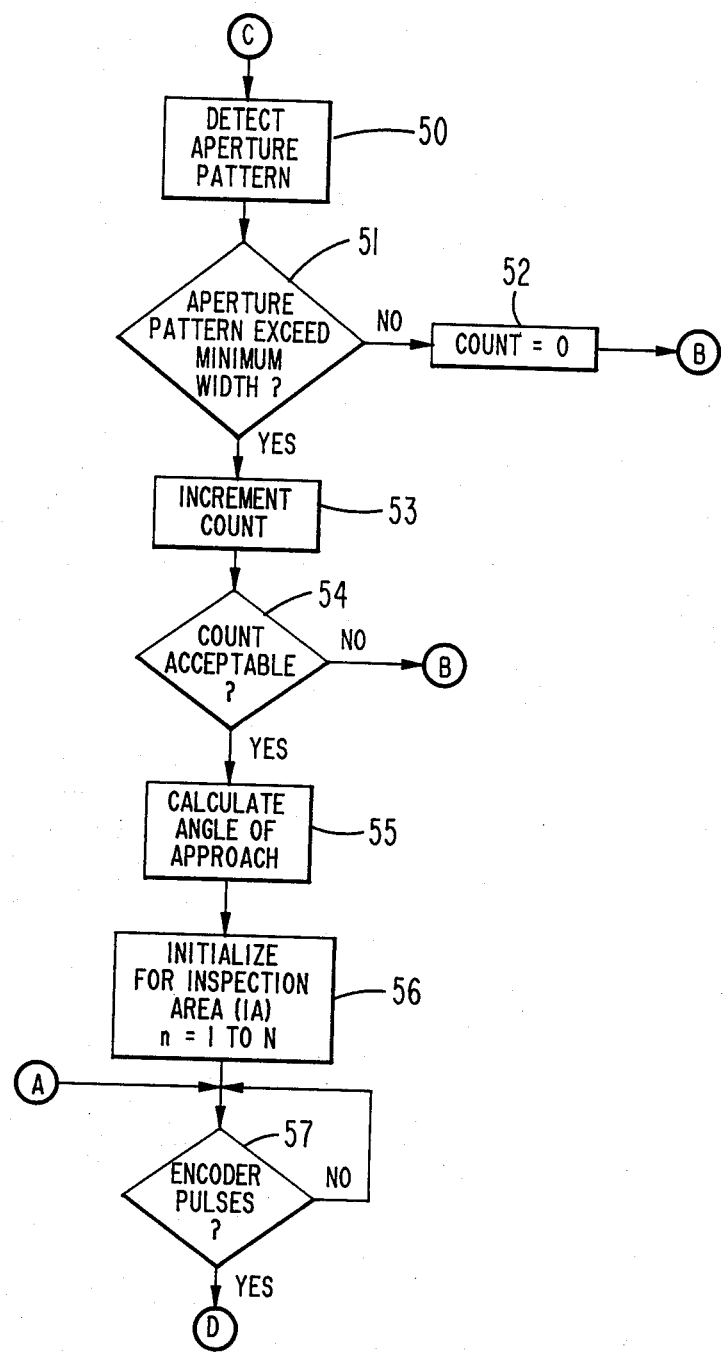

In FIG. 5b, when an aperture pattern exists between light source 21 and the upper CCD 16 the leading edge of the aperture pattern is detected at step 50. The width of the aperture pattern is checked at step 51 to distinguish the aperture pattern through which the light passed from other apertures, such as completely etched through corners, or flaws and tears in the strip 11. When the aperture width is not sufficient to suggest the presence of an aperture pattern, step 52 is entered to reset the counter to zero and re-enter step 46 of FIG. 5a. When the aperture pattern width exceeds the minimum width, the presence of an aperture pattern 12 is suggested and step 53 is entered to increment the counter. The acceptability of the count is then verified at step 54. The verification of the presence of an aperture pattern requires a minimum number of scans at step 54. Step 54 verifies that the required minimum number of scans has occurred. As shown in FIG. 3, the number of count pulses required for the alignment of an inspection area 18 and the CCD 16 is known. Accordingly, a convenient minimum number of count pulses to be received from the encoder 19 subsequent to the detection of the leading edge of the aperture pattern is used at 54 to verify the presence of the aperture pattern. When the needed count has not been met, step 46 is re-entered to increment the counter one count. When an aperture pattern has come into alignment with the CCD 16, step 55 is entered to calculate the angle of approach. The angle of approach is calculated by noting the difference in the location of the center of the strip 11 for the first and last inspection areas of the preceeding aperture pattern and by dividing this difference by the longitudinal distance between the same two inspection areas for the preceeding aperture pattern. Step 56 is then entered to initialize the system for all of the inspection areas 18. The presence of the encoder pulses is again verified at step 57.

Figure 5C:
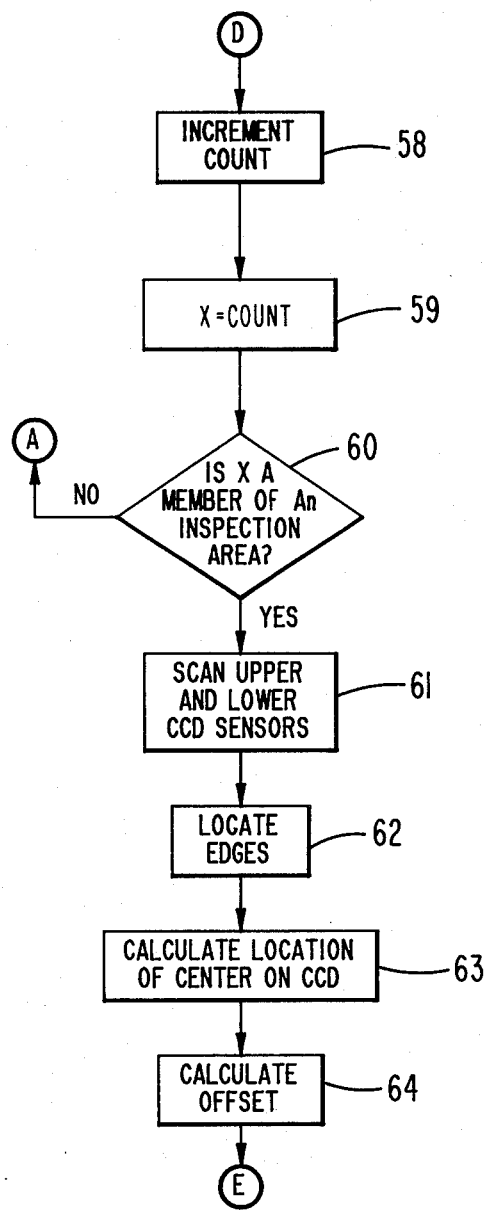

In FIG. 5c at step 58, the counter is again incremented and at step 59 the count is incremented to the next longitudinal count X. Step 60 verifies that the particular count pulse represents an X, longitudinal, location within one of the inspection areas. When it is not, step 57 is re-entered and the process repeated back to step 60. When an inspection area is aligned with the CCD 16, step 61 is entered and both the CCD 16 and CCD 21 are simultaneously scanned. Step 62 is then entered to locate the longitudinal edges of the aperture pattern 12. The location of the center of the aperture pattern 12 with respect to the center pixel 33 of the CCD 16 is calculated at step 63. When the actual center of the portion 32 of the waveform 25 (FIG. 4) is on a pixel different from pixel 33, the number of pixels between the actual and optimum positions is used to calculate the offset. This calculation is performed at step 64.

Figure 5D:
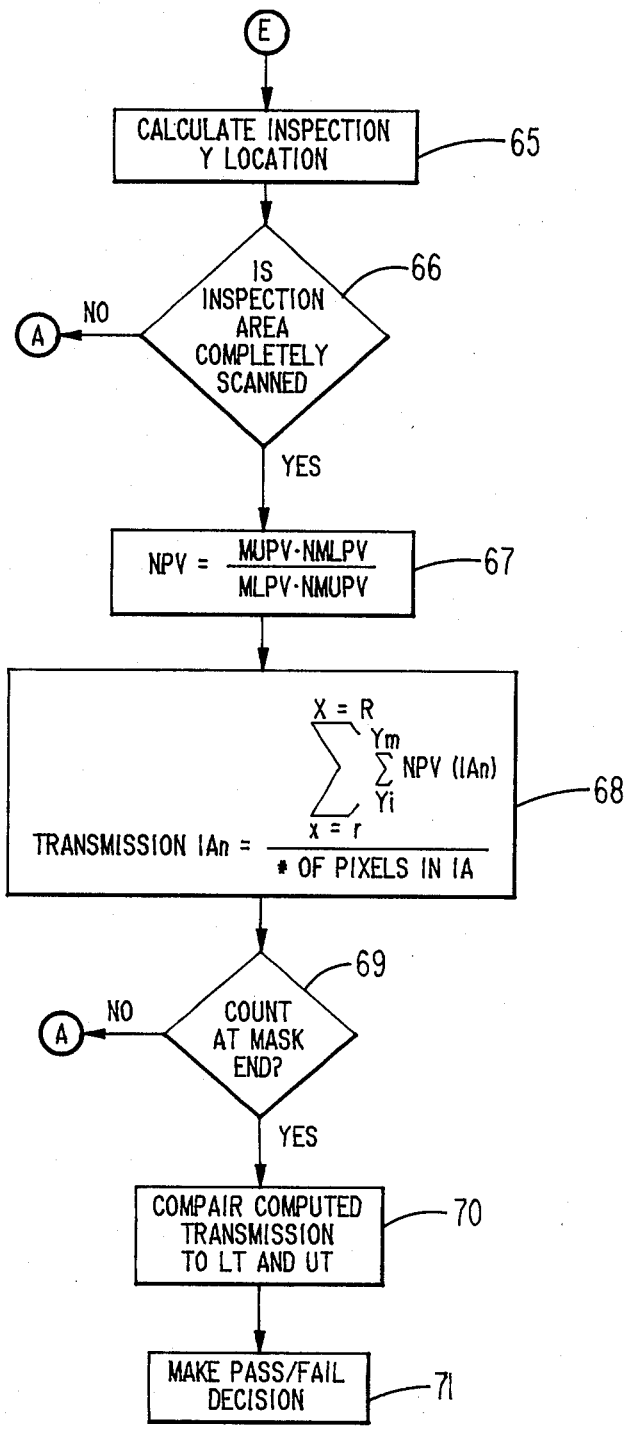

In FIG. 5d, the offset is used to calculate the transverse, Y, location of the aperture pattern at step 65. In FIG. 3, the pixels which are to be considered for a portion of a particular inspection area have known transverse, Y, positions. When the strip 11 is not centered with respect to the CCD 16, the offset is used to select different pixels to effectively shift the sensor by the offset whereby pixels which are within the inspection area are considered. Step 66 is then entered to determine whether or not one of the inspection areas has been completely scanned. When it has not, step 57, of FIG. 5b, is reentered to repeat the process for the next portion of the inspection area. When the inspection area is completely scanned, steps 67 and 68 are entered to, respectively, calculate the normalized pixel value NPV and the transmission IA for the inspection area in accordance with the expressions:

$$NPV = \frac{MUPV \cdot NMLPV}{MLPV \cdot NMUPV} \text{ where:} \quad (1)$$

NPV = normalized pixel value
MUPV = upper pixel value with mask
NMLPV = lower pixel value with no mask
MLPV = lower pixel value with mask
NMUPV = upper pixel value with no mask.

The NMLPV and NMUPV factors set a system ratio to compensate for changes in the light or optical system. The ratio is determined by simultaneously scanning both CCD's 16 and 23 without a mask. The difference in response then is a normalizing ratio which is set into the system prior to making any measurements. Any light or optical changes will have the same affect on both CCD's 16 and 23 and the ratio remains constant.

The transmission of the measured area is then calculated using the expression:

$$IA = \frac{\sum\limits_{X=r}^{X=R} \sum\limits_{Yi}^{Ym} NPV(IAn)}{IAP} \text{ where:} \quad (2)$$

IA = Transmission of the area being measured
r-R = The number count pulses along the longitudinal, X, axis of the inspection area
Yi-Ym = The number of pixels along the transverse, Y, axis of the inspection area portion
NPV = Normalized pixel value
IAn = The indicated pixel number
IAP = Number of pixels in the inspection area.

After the normalized transmission of the inspection area under consideration is completed, step 69 is entered to determine whether or not a complete aperture pattern has been measured. When a complete pattern has not been measured, step 57 is reentered to repeat the process for the next inspection area. When all inspection areas have been considered step 70 is entered to compare the measured transmission capability to the upper, UT, and lower, LT, transmission capabilities set into the system at step 44. Step 71 is then entered to make a pass/fail decision. The pass/fail decision can be factory determined and thus can vary for each type of aperture pattern. The decision can be based upon a consideration of the transmission capabilities of all of the inspection areas simultaneously. Alternatively, the mask can be failed if any one of the inspection areas fails to fall within the transmission limits.

What is claimed is:

1. A system for measuring energy transmission through an aperture pattern in a longitudinally moving opaque strip of material, comprising:
   means for scanning energy transversely across said strip;
   a CCD (charge coupled device) sensor having at least one row of pixels arranged substantially perpendicular to said strip, and having at least one pixel centered over said strip when said strip is located at an optimum location; said CCD being positioned to receive said energy through said apertures;

means for defining inspection areas within said aperture pattern where energy transmission through said aperture pattern is measured;

said inspection areas being defined by preselected pixels of said CCD when said CCD is scanned by energy passing through said inspection areas;

encoder means responsive to said longitudinal motion for providing count pulses;

counter means responsive to said count pulses, said inspection areas being scanned by said energy on preselected counts, whereby the energy levels on said preselected CCD pixels is indicative of energy transmission through said aperture patterns; and adder means responsive to said preselected pixel levels for adding said pixel levels for each of said inspection areas, and providing the energy transmission through each of said inspection areas.

2. The system of claim 1 further including means for calculating the offset between the center of said strip and said center pixel and for changing from some of said preselected pixels to new preselected pixels to accommodate for said offset.

3. The system of claim 2 further including means for calculating the angular disposition of said strip with respect to said row of CCD pixels.

4. The system of claim 3 wherein said inspection areas are circles, whereby the number of pixels considered for consecutive counts varies in accordance with the radius of said circles.

5. The system of claim 4 wherein said means for scanning further includes another CCD sensor arranged to receive energy directly, and wherein said system includes divider means for establishing a system ratio of CCD energy response through said aperture patterns to direct CCD energy response.

6. The system of claim 5 wherein said CCD is a linear array.

7. The system of claim 6 wherein said adder means adds said pixel levels in accordance with the expression:

$$IA = \frac{\sum\limits_{X=r}^{X=R} \sum\limits_{Yi}^{Ym} NPV(IAn)}{IAP} \quad \text{where:} \tag{2}$$

IA = Transmission of the area being measured
r-R = The number count pulses along the longitudinal, X, axis of the inspection area
Yi-Ym = The number of pixels along the transverse, Y, axis of the inspection area portion
NPV = Normalized pixel value
IAn = The indicated pixel number
IAP = Number of pixels in the inspection area.

8. The system of claim 3 wherein said means for scanning further includes another CCD sensor arranged to receive energy directly, and wherein said system includes divider means for establishing a system ratio of CCD energy response through said aperture pattern to direct CCD energy response.

9. The system of claim 8 wherein said adder means adds said pixel levels in accordance with the expression:

$$IA = \frac{\sum\limits_{X=r}^{X=R} \sum\limits_{Yi}^{Ym} NPV(IAn)}{IAP} \quad \text{where:} \tag{2}$$

IA = Transmission of the area being measured
r-R = The number count pulses along the longitudinal, X, axis of the inspection area
Yi-Ym = The number of pixels along the transverse, Y, axis of the inspection area portion
NPV = Normalized pixel value
IAn = The indicated pixel number
IAP = Number of pixels in the inspection area.

10. The system of claim 9 wherein said CCD is a linear array.

11. A method of measuring energy transmission through an aperture pattern in a longitudinally moving opaque strip of material comprising the steps:

scanning energy transversely across said strip;

detecting energy passing through said aperture pattern with a CCD sensor having a row of pixels substantially perpendicular to the longitudinal axis of said strip and having a pixel transversely centered with respect to the optimum position of said strip;

providing a series of count pulses in response to the longitudinal motion of said strip;

defining a plurality of inspection areas in said aperture pattern, one axis of said areas being defined by particular pixels of said CCD for a particular one of said count pulses whereby said particular pixels constitute one transverse line of an inspection area, the other axis of said areas being defined by a preselected number of said count pulses, whereby said count pulses define the longitudinal axis of said areas; and summing the change levels on the pixels within said inspection areas to calculate the energy transmission through said inspection areas.

12. The method of claim 11 further including the step of determining the offset of the center of said strip with respect to said centered pixel and substituting other pixels for some of said particular pixels to compensate for said offset.

13. The method of claim 12 further including the step of calculating the angular displacement of the longitudinal axis of said strip with respect to the optimum longitudinal axis of said strip.

14. The method of claim 13 further including the step of normalizing said transmission measurement by; directly scanning another CCD with said energy, and dividing the output of the CCD scanned through said aperture pattern by the output of said directly scanned CCD.

15. The method of claim 14 wherein the step of summing is accomplished in accordance with the equation $$IA = \frac{\sum\limits_{X=r}^{X=R} \sum\limits_{Yi}^{Ym} NPV(IAn)}{IAP} \quad \text{where:} \tag{2}$$

IA = Transmission of the area being measured
Y-R = The number count pulses along the longitudinal, X, axis of the inspection area
Yi-Ym = The number of pixels along the transverse, Y, axis of the inspection area portion
NPV = Normalized pixel value
IAn = The indicated pixel number
IAP = Number of pixels in the inspection area.

16. The method of claim 15 wherein said, inspection areas are circles and said energy is light.

17. The method of claim 12 wherein said offset is determined detecting the CCD pixels corresponding to the edges of said strip and dividing by two to identify the actually centered pixel and comparing said actually centered pixel to said transversely centered pixel.

18. The method of claim 17 further including the step of calculating the angular displacement of the longitudinal axis of said strip with respect to the optimum longitudinal axis of said strip.

19. The method of claim 18 wherein said angular displacement is calculated by finding the distance between said actually centered pixel for the first and last of said inspection areas and by dividing said difference by the longitudinal spacing between the first and last inspection areas.

20. The method of claim 19 further including the step of normalizing said transmission measurement by; directly scanning another CCD with said energy, and dividing the output of the CCD scanned through said aperture pattern by the output of said directly scanned CCD.

21. The method of claim 20 wherein the step of summing is accomplished in accordance with the equation $$IA = \frac{\sum_{X=r}^{X=R} \sum_{Y_i}^{Y_m} NPV(IAn)}{IAP} \quad (2)$$

where:

IA = Transmission of the area being measured
Y-R = The number count pulses along the longitudinal, X, axis of the inspection area
Yi-Ym = The number of pixels along the transverse, Y, axis of the inspection area portion
NPV = Normalized pixel value
IAn = The indicated pixel number
IAP = Number of pixels in the inspection area.

* * * * *